(12) United States Patent
Gordon (10) Patent No.: US 7,033,747 B2
(45) Date of Patent: Apr. 25, 2006

(54) MULTI-PARAMETER ASSAYS INCLUDING ANALYSIS DISCS AND METHODS RELATING THERETO

(75) Inventor: John Francis Gordon, Irvine, CA (US)

(73) Assignees: Nagaoka & Co., LTD, (JP); Burstein Technologies, Inc., CA (US)

(*) Notice: Subject to any disclaimer, the term of this patent is extended or adjusted under 35 U.S.C. 154(b) by 0 days.

(21) Appl. No.: 10/121,281

(22) Filed: Apr. 11, 2002

(65) Prior Publication Data

US 2002/0151043 A1    Oct. 17, 2002

Related U.S. Application Data

(60) Provisional application No. 60/283,213, filed on Apr. 11, 2001.

(51) Int. Cl.
*C12Q 1/68* (2006.01)

(52) U.S. Cl. .............................................. 435/4; 435/6

(58) Field of Classification Search ................ 422/72, 422/73, 74; 435/4, 6
See application file for complete search history.

(56) References Cited

U.S. PATENT DOCUMENTS

| | | |
|---|---|---|
| 3,437,266 A | 4/1969 | Patterson |
| 3,555,284 A | 1/1971 | Anderson |
| 3,736,432 A | 5/1973 | Sweet |
| 3,791,932 A | 2/1974 | Schuurs et al. |
| 3,798,459 A | 3/1974 | Anderson et al. |
| 3,854,508 A | 12/1974 | Burtis et al. |
| 3,873,217 A | 3/1975 | Anderson et al. |
| 3,890,101 A | 6/1975 | Tiffany et al. |
| 3,901,658 A | 8/1975 | Burtis et al. |
| 3,966,322 A | 6/1976 | Greaves et al. |
| 4,233,402 A | 11/1980 | Maggio et al. |
| 4,284,602 A | 8/1981 | Kelton et al. |
| 4,456,581 A | 6/1984 | Edelmann et al. |
| 4,469,793 A | 9/1984 | Guigan |
| 4,478,768 A | 10/1984 | Takeoka et al. |
| 4,483,925 A | 11/1984 | Noack |
| 4,596,695 A | 6/1986 | Cottingham |
| 4,608,344 A | 8/1986 | Carter et al. |
| 4,835,106 A | 5/1989 | Johnson et al. |
| 4,876,557 A | 10/1989 | Yabe |
| 4,900,513 A | 2/1990 | Barker et al. |
| 5,041,266 A | 8/1991 | Fox |
| 5,061,381 A | 10/1991 | Burd |
| 5,160,702 A | 11/1992 | Kopf-Sill et al. |
| 5,167,922 A | 12/1992 | Long |
| 5,173,193 A | 12/1992 | Schembri |
| 5,173,262 A | 12/1992 | Burtis et al. |
| 5,186,844 A | 2/1993 | Burd et al. |
| 5,256,376 A | 10/1993 | Callan et al. |
| 5,265,169 A | 11/1993 | Ohta et al. |
| 5,270,210 A | 12/1993 | Weyrauch et al. |
| 5,310,523 A | 5/1994 | Smethers et al. |
| 5,376,252 A | 12/1994 | Ekström et al. |
| 5,409,665 A | 4/1995 | Burd |
| 5,445,934 A | 8/1995 | Fodor et al. |
| 5,472,603 A | 12/1995 | Schembri |
| 5,545,540 A | 8/1996 | Mian |
| 5,565,105 A | 10/1996 | Thakor |
| 5,580,790 A | 12/1996 | Wall et al. |
| 5,585,069 A | 12/1996 | Zanzucchi et al. |
| 5,591,643 A | 1/1997 | Schembri |
| 5,631,166 A | 5/1997 | Jewell |
| 5,684,774 A | 11/1997 | Yamamuro |
| 5,700,655 A | 12/1997 | Croteau et al. |
| 5,732,066 A | 3/1998 | Moriya et al. |
| 5,792,654 A | 8/1998 | Bohannon et al. |
| 5,807,522 A | 9/1998 | Brown et al. |
| 5,837,552 A | 11/1998 | Cotton et al. |
| 5,843,767 A | 12/1998 | Beattie |
| 5,882,903 A | 3/1999 | Andrevski et al. |
| 5,882,930 A | 3/1999 | Baier |
| 5,892,577 A | 4/1999 | Gordon |
| 5,900,481 A | 5/1999 | Lough et al. |

(Continued)

FOREIGN PATENT DOCUMENTS

EP        0297 394 A2    1/1989

(Continued)

OTHER PUBLICATIONS

Phan et al., U.S. Appl. No. 60/253,283.*

(Continued)

*Primary Examiner*—Leon B. Lankford, Jr.
*Assistant Examiner*—Ruth A. Davis
(74) *Attorney, Agent, or Firm*—Knobbe, Martens, Olson & Bear, LLP (57) ABSTRACT

Methods and apparatus for testing a sample for target molecules or chemicals. The apparatus includes a rotatable optical disc having a reaction chamber and having at least two groups of beads or micro-particles, the different group of beads having at least two different densities, sizes, shapes, and/or color, and each bead in a group having different probes attached thereto. A sample is added to the reaction chamber and the disc is rotated. The reaction chamber has a density gradient medium that causes beads of different densities to remain at different radial locations, depending on the density of the beads. The beads are then inspected by directing a beam of electromagnetic radiation onto the disc. The beam may be reflected from or transmitted through the disc. The amount, or presence, or absence of targets is determined by analyzing the signal returned from the beam. Related methods of performing assays and making the disc apparatus are provided.

17 Claims, 7 Drawing Sheets

U.S. PATENT DOCUMENTS

| | | |
|---|---|---|
| 5,922,617 A | 7/1999 | Wang et al. |
| 5,955,352 A | 9/1999 | Inoue et al. |
| 6,013,513 A | 1/2000 | Reber et al. |
| 6,027,695 A | 2/2000 | Oldenburg et al. |
| 6,027,873 A | 2/2000 | Schellenberger et al. |
| 6,030,581 A | 2/2000 | Virtanen |
| 6,063,589 A | 5/2000 | Kellogg et al. |
| 6,117,630 A | 9/2000 | Reber et al. |
| 6,143,248 A | 11/2000 | Kellogg et al. |
| 6,159,689 A | 12/2000 | Parton |
| 6,238,869 B1 | 5/2001 | Kris et al. |
| 6,302,134 B1 | 10/2001 | Kellogg et al. |
| 6,387,331 B1 | 5/2002 | Hunter |
| 6,399,361 B1 | 6/2002 | Brotherston et al. |
| 2001/0001060 A1 | 5/2001 | Kellogg et al. |
| 2001/0055812 A1* | 12/2001 | Mian et al. .................. 436/45 |
| 2002/0076354 A1 | 6/2002 | Cohen |
| 2002/0106786 A1* | 8/2002 | Carvalho et al. ........ 435/287.3 |
| 2002/0163642 A1 | 11/2002 | Zoval et al. |
| 2002/0196435 A1 | 12/2002 | Cohen et al. |
| 2003/0003464 A1* | 1/2003 | Phan et al. .................... 435/6 |

FOREIGN PATENT DOCUMENTS

| | | |
|---|---|---|
| EP | 0 392 475 | 10/1990 |
| EP | 0 417 305 A1 | 3/1991 |
| EP | 0 435 246 A2 | 7/1991 |
| EP | 0 504 432 | 9/1992 |
| EP | 0 521 421 A2 | 1/1993 |
| EP | 0 608 006 B1 | 7/1994 |
| EP | 0 693 560 A2 | 1/1996 |
| GB | 1 557 984 | 12/1979 |
| GB | 2 147 100 A | 5/1985 |
| WO | WO 94/29484 | 12/1994 |
| WO | WO 95/25815 | 9/1995 |
| WO | WO 95/33986 | 12/1995 |
| WO | WO 96/17959 | 6/1996 |
| WO | WO 96/32841 | 10/1996 |
| WO | WO 97/21090 | 6/1997 |
| WO | WO 98/01533 | 1/1998 |
| WO | WO 98/07019 | 2/1998 |
| WO | WO 98/53311 | 11/1998 |
| WO | WO 99/35499 | 7/1999 |
| WO | WO 99/58245 | 11/1999 |
| WO | WO 01/02737 A1 | 1/2001 |
| WO | WO 01/87485 A2 | 11/2001 |

OTHER PUBLICATIONS

Phan et al., U.S. Appl. No. 60/253,958.*
Phan et al., U.S. Appl. No. 60/272,525.*
Phan et al., U.S. Appl. No. 60/257,806.*
Price et al., "Centrifugal Analysers in Clinical Chemistry", Praeger Special Studies, Praeger Scientific 1980, pp. 1-27.

* cited by examiner

MULTI-PARAMETER ASSAYS INCLUDING ANALYSIS DISCS AND METHODS RELATING THERETO

CROSS-REFERENCE TO RELATED APPLICATIONS

This application claims the benefit of priority from U.S. Provisional Application Ser. No. 60/283,213 filed Apr. 11, 2001, which is incorporated herein by reference in its entirety.

BACKGROUND OF THE INVENTION

1. Field of the Invention

The present invention relates to an apparatus for performing assays in conjunction with an optical bio-disc. The invention further relates to methods for separating, immobilizing and/or detecting micro-particles or beads, cells, labels, or tags using a density gradient and/or centrifugation to perform an assay 2. Discussion of Background Art and the Present Invention There is a significant need to make diagnostic assays and forensic assays of all types faster and more local to the end-user. Ideally, clinicians, patients, investigators, the military, other health care personnel, and consumers should be able to test themselves for the presence of certain factors or indicators in their systems, and for the presence of certain biological material at a crime scene or on a battlefield. At present, there are a number of silicon-based chips with nucleic acids and/or proteins attached thereto, which are commercially available or under development, for performing biomedical, chemical, or biochemical assays. These chips are not for use by the end-user, or for use by persons or entities lacking very specialized expertise and expensive equipment. It is an object of the present invention to obviate or mitigate at least one of these disadvantages by use of a relatively inexpensive assay system that can be used by the end user without specialized training.

Many biochemical techniques exploit the mutual interaction of antigens and antibodies, hybridization between complementary strands of DNA, or protein affinity. Some of these may include streptavidin and biotin, along with the use of labeled reagents. A variety of labels or tags have been employed for detection. Examples include enzymes, color-based, radioactive, phosphorescent, fluorescent and chemiluminescent reagents, microspheres, metal colloids, as well as fluorescent dyes such as fluorescein and rhodamine. Fluorescent anti-human IgG, for example, is routinely used as a labeled reagent.

A "sandwich" immunoassay is performed in one embodiment of the present invention wherein a doubled layer procedure is designed to detect a specific antibody or antigen. For example, to detect the presence of an antibody in a sample, a corresponding antigen is first immobilized onto solid substrate. The immobilized antigen is then exposed to the sample being tested. Some or all of the antibodies present will bind to the immobilized antigen. Any excess or unbound antibody is washed away.

A labeled reagent such as fluorescent anti-IgG is then added to the sample. The labeled reagent binds to the antibody and any excess reagent is washed away. The intensity of the fluorescence is then measured to provide an indication of the quantity of antibody present in the sample.

One of the problems with "sandwich" immunoassays is that a number of washing steps are involved. The washing steps are necessary to remove the excess antibodies and labeled reagents, which would otherwise have an adverse effect on the accuracy of the results.

A further problem is that a sample may only be analyzed for one target at a time. Therefore, to detect a number of different targets in a sample, separate sample containers are required. As a consequence, a large number of washing steps are necessary, making the procedure cumbersome and time-consuming.

It is an object of the present invention to obviate or mitigate at least one of the abovementioned disadvantages.

It is a further object of the present invention to reduce or eliminate the number of washing steps that are presently required to conduct an immunoassay.

The objectives mentioned above are achieved by providing a device for conducting a chemical, biochemical, or biomedical assay that is adapted to be used in conjunction with a disc-based scanning device. One such device is described, for example, in U.S. Pat. No. 5,892,577, entitled "Apparatus and Method for Carrying out Analysis of Samples", which is incorporated herein by reference in its entirety.

SUMMARY OF THE INVENTION

The present invention relates to performing assays, and particularly to using beads of various densities on a disc. individually or in a complex. The invention includes methods for separating and detecting beads or micro-particles, complexes of beads, tags, labels, or cells attached to the beads, discs for performing assays, and related detection systems.

According to a first aspect of the present invention, there is provided a device for conducting an assay. This device includes a rotatable disc which defines at least one reaction chamber and at least one separation chamber. The reaction chamber is coupled to the separation chamber or channel via a controllable barrier means. A density gradient forming medium is located in the separation chamber so that in use, a plurality of particles having different densities may be separated along the density gradient of the medium.

In a second aspect of the present invention, there is provided another device for conducting an assay. This particular device includes a rotatable disc which defines at least one separation chamber. The separation chamber or channel contains a density gradient forming medium and in use, a plurality of particles having different buoyant densities may be separated along the density gradient of the medium.

The rotatable disc is adapted to rotate about its central aperture which is adapted to releasably engage with a rotatable shaft. Preferably also, the disc defines a plurality of radially extending reaction chambers and separation chambers. A cover disc is used to complete the reaction chamber and is formed of a light transmitting material, for example, a clear plastic material.

The base of the rotatable disc may be a compact disc (CD), a recordable CD (CD-R), CD-RW, a digital versatile disc (DVD), DVD-R, DVD-RW, or other standard or specialized optical disc format including fluorescent and magneto-optical discs.

The separation chamber or channel is provided with a density gradient forming medium. An example of a suitable medium is a gel provided by Pharmacia Biotech under the trademark Percoll. The density gradient may be pre-formed in the gel, or generated by the application of a centripetal force. In one embodiment of the invention, the density gradient is formed and maintained by rotating the disc about its central axis. Advantageously, the density gradient medium is transparent or transmissive to light.

During use of the disc device, a plurality of micro-particles having different densities and/or size is introduced into the reaction chamber. Suitable micro-particles include density marker beads available from Pharmacia Biotech. Preferably, the beads are of pre-determined densities and size. The beads may also be color-coded or fluorescent for identification purposes.

When the disc is rotated and the controllable barrier member is actuated, the beads or micro-particles can move from the reaction chamber under centripetal force. When a micro-particle reaches a point along the separation chamber or channel where the density of the micro-particle equals that of the surrounding medium, it comes to rest. When this occurs, the micro-particle or bead is said to have reached its isopycnic point.

The minimum density of the micro-particles is greater than the minimum density of the density gradient medium. Accordingly, upon equilibration, no particles will be left in the reaction chamber.

In one particular embodiment of the present invention, specific antigens and/or antibodies, may be immobilized onto the surface of the beads. For example, to analyze a sample for a selection of antibodies, a corresponding selection of antigens may be immobilized onto beads of a particular density.

As noted above, antibodies and antigens may be used for the detection of each other. An antibody will bind selectively to its corresponding antigen and the bound species may be identified by using a label or "tag". A labeled reagent of, for example, a fluorescent anti-IgG may be used. Fluorescent anti-IgG will bind to an epitope on the target antibody. Accordingly, the resulting complex may be identified by the optical properties of the anti-IgG label.

In another embodiment of the present invention, a reaction chamber is loaded with fluorescent anti-IgG and at least two groups of beads or micro-particles, each group having different densities and antigens attached thereto. A sample of, for example, blood or serum, is then introduced into the reaction chamber. Antibodies in the sample may complex with both the immobilized antigens and the fluorescent anti-IgG.

In yet another embodiment of the present invention, binding partners, including at least two micro-particles of different pre-determined densities, shapes, and/or sizes, are loaded into the reaction chamber. Each micro-particle or binding partner has attached thereto at least one antibody that has affinity to the antigen of interest or target antigen. The antibody attached to each particular micro-particle has specific affinity to a different epitope on the target antigen. When a sample containing the target antigen is introduced to the reaction chamber, the sample them complexes with both immobilized antibodies on the different binding partners thus forming a binding partner micro-particle complex. As would be apparent to one of skill in the art given the present disclosure, the bead complexing is not limited to two beads or binding partners but may be performed in a multi-particle or multi-parameter test format involving three or more micro-particles of different densities, shapes, and/or sizes.

In still another embodiment of the present invention, the binding partners may include at least one bead or micro-particle of known density and one cell wherein the bead would have attached thereto at least one antibody that binds to at least one epitope on a surface marker of the cell. So when the cell and the bead are mixed in the reaction chamber, a cell-bead complex is formed by the binding of the antigen on the bead to the cell surface marker. The complexing reaction is not limited to a single cell or bead but multiple cells may bind to a single bead or multiple beads to a single cell. The bead may contain one or more types of anitibodies having affinity to surface markers on different cells. Cell surface markers may include cluster designation markers, cell surface proteins, cell surface glycoproteins, sugars, or any substance on a cell surface that can be recognized or can bind to an antibody.

In another embodiment of the present invention, multiplexing assays may be carried out using multiple binding partners including beads or micro-particles, cells, and tags in any combination to form complexes including at least two binding partners to create a multi-parameter test. The micro-particles and/or cells have different physical properties as advantageously employed in the present invention. These properties may include, for example, a difference in density, size, mass, shape, color, and/or surface properties.

Complexing reactions, in the reaction chamber, may take place whilst the disc is rotating. Alternatively, the rotation may be commenced once the complexing reactions are completed. In either case, rotation serves to form and/or maintain a density gradient along the length of the separation chamber. The complexing reactions may also be carried out outside the disc then loaded into the reaction chamber for analysis.

Once a density gradient is established, the controllable barrier is removed. The centripetal force generated by the rotation causes the beads or micro-particles to move from the reaction chamber to the separation chamber. The target of interest, being coupled to a bead or beads, is also transported from the reaction chamber to the separation chamber. The beads, bead complexes, or bead-cell complexes by virtue of having different densities, will come to rest at different positions along the length of the separation chamber. Details regarding one embodiment of the various components of the related optical bio-disc are described below in conjunction with the drawing figures.

As explained above, beads with the antibodies of interest bound thereto are tagged or labeled, or bound in a complex of two or more beads, or two or more bead-cell complexes. Thus, they may be located or detected by optical means as described below in further detail.

The unbound and/or unreacted materials in the reaction chamber are not drawn into the separation chamber or channel by the centripetal force. This is because the density of the unbound and/or unreacted materials is less than the minimum density of the density gradient medium. Accordingly, the materials of interest may be separated from the bulk of the reaction mixture without the need for cumbersome washing steps.

Once separated, the position of the various beads, bead complexes, or bead-cell complexes may be measured by using a disc-based scanning device. Applicant's U.S. Pat. No. 5,892,577 describes a scanning device that may be used in conjunction with the present invention.

Whilst the disc is rotating, a beam of electromagnetic radiation may be scanned over the surface of the disc. The beam is transmitted through the light transmitting cover of the disc, and interacts with the material in the separation chamber. As indicated below, the disc may include multiple separation chambers each supplied with the same or different samples. The interacted or "modulated" beam is detected and analyzed. The analysis provides information on the position of the beam, as well as information on the nature of the material under analysis. The labeled beads, complexed beads, or bead-cell complexes interact with the incident beam in a characteristic manner to produce a characteristic modulated signal. Thus, by monitoring where such modulated signals occur, and comparing these signals to those of a calibrated control, the identity of specific targets present in a sample may be determined. By measuring the intensity of such signals, the quantity of the specific targets may also be deduced.

The device of the present invention may also be used to provide a control against which the results of any of the assays described above may be compared.

According to a third aspect of the present invention, there is provided a method for conducting an assay. This method includes the steps of (1) providing a rotatable disc which defines at least one reaction chamber and at least one separation chamber, the reaction chamber being coupled to the separation chamber or channel via controllable barrier means, and the separation chamber having a density gradient forming medium; (2) introducing a plurality of particles having different pre-determined densities, shapes, sizes, and/or color into the reaction chamber, the particles being adapted to receive specific reagents; (3) introducing a sample under test into the reaction chamber; (4) rotating the disc to provide a centripetal force; (5) controlling the controllable barrier between the reaction and separation chambers, so that the plurality of particles can move from the reaction chamber to the separation chamber under the centripetal force to separate the particles according to density; and (6) analyzing the contents of the separation chamber or channel by optical means.

The method may further include the step of introducing a labeled reagent into the reaction chamber prior to rotating the disc. Alternatively, a labeled reagent may be mixed with the test sample, prior to introducing the mixture into the reaction chamber.

Other features and advantages of the different embodiments and aspects of the present invention will become apparent from the following detailed description and accompanying drawing figures.

BRIEF DESCRIPTION OF THE DRAWING FIGURES

Further objects of the present invention together with additional features contributing thereto and advantages accruing therefrom will be apparent from the following description of preferred embodiments of the present invention which are shown in the accompanying drawing figures with like reference numerals indicating like components throughout, wherein.

DETAILED DESCRIPTION OF THE PREFERRED EMBODIMENTS

Figure 1:
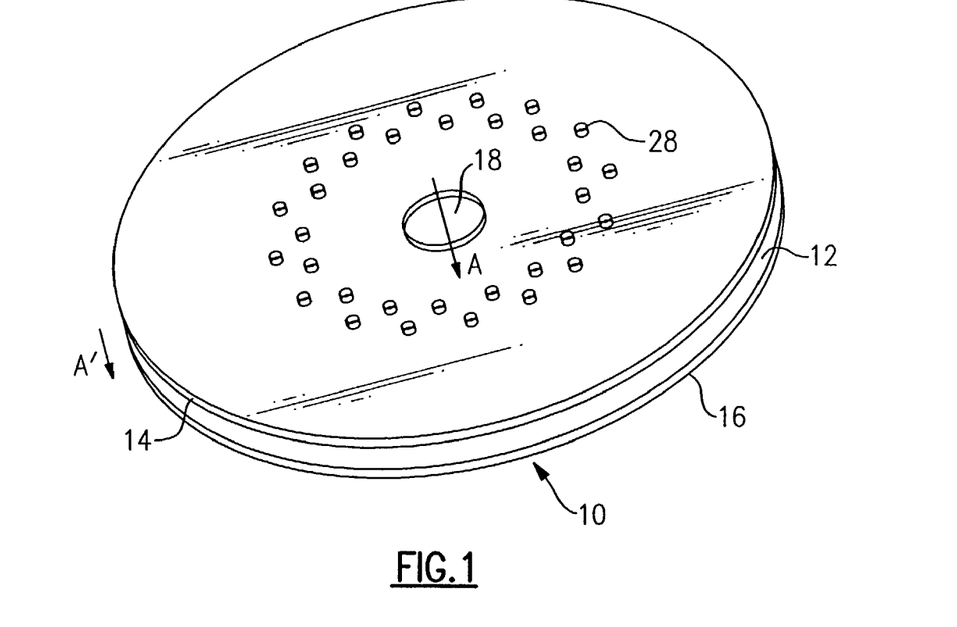
FIG. 1 is a perspective view of a disc in accordance with one embodiment of the present invention.
Figure 2:
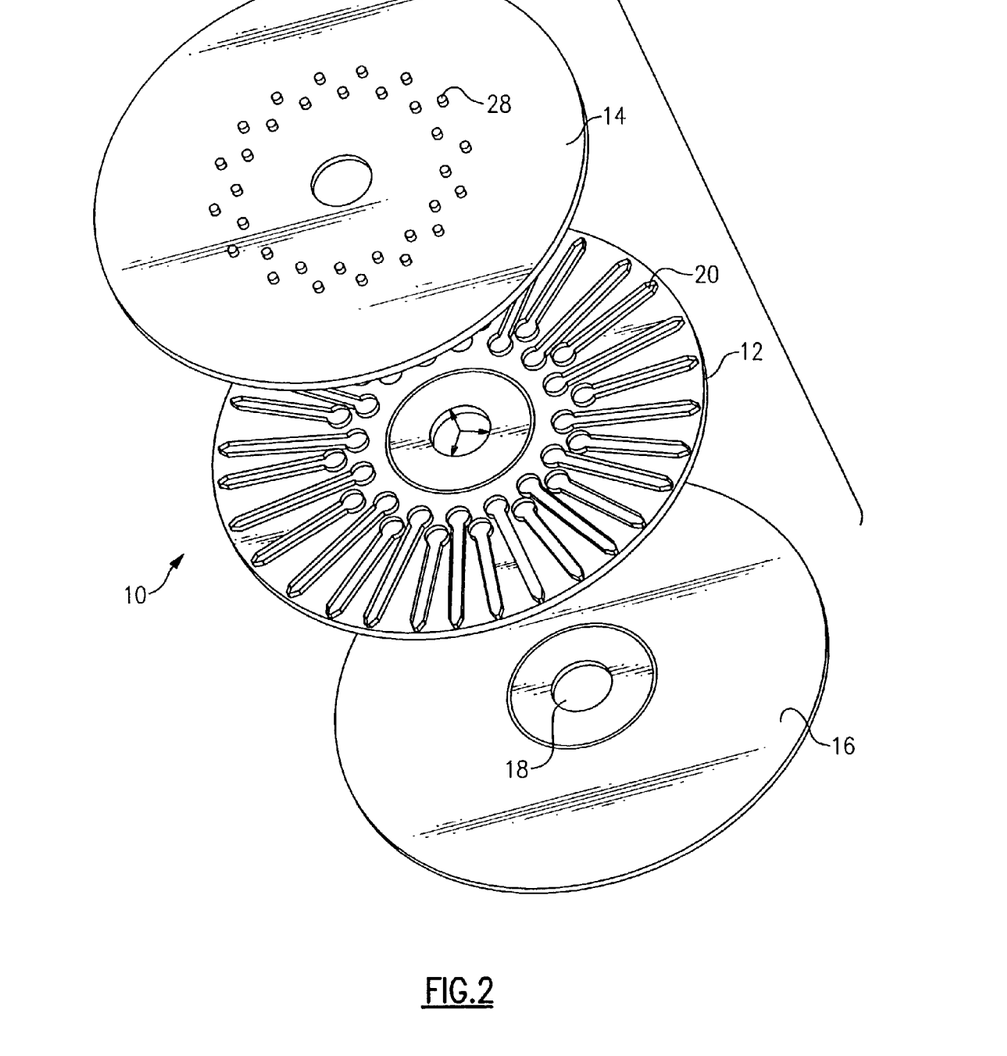
FIG. 2 is an exploded perspective view of the disc of FIG. 1.

Reference is first made to FIGS. 1 and 2 of the drawing that depict a device in accordance with an embodiment of the present invention. The device is adapted to be used in conjunction with an optical disc-based scanning device, such as that described in U.S. Pat. No. 5,892,577, which is incorporated in its entirety herein.

As shown in FIGS. 1 and 2, the device includes a disc 10 composed of a body 12 disposed between a cover 14 and a base 16. The body 12, cover 14, and base 16 are bonded together to form an integral disc such as that illustrated in FIG. 1. The base 16 may be a compact disc (CD), a recordable CD (CD-R), CD-RW, a digital versatile disc (DVD), DVD-R, DVD-RW, or other standard or specialized optical disc format including fluorescent and magneto-optical discs. The cover 14 may be formed of a clear plastic material including, for example, polycarbonate. Alternatively, the disc may be assembled in a reverse manner wherein the cover 14 is a compact disc (CD), a recordable CD (CD-R), CD-RW, a digital versatile disc (DVD), DVD-R, DVD-RW, or any equivalent optical disc format. In this embodiment, the base 16 is formed of a transparent material. The disc 10 is provided with a central hole 18, FIG. 1, that is adapted to releasably engage with, for example, a rotating shaft or spindle.

Figure 3:
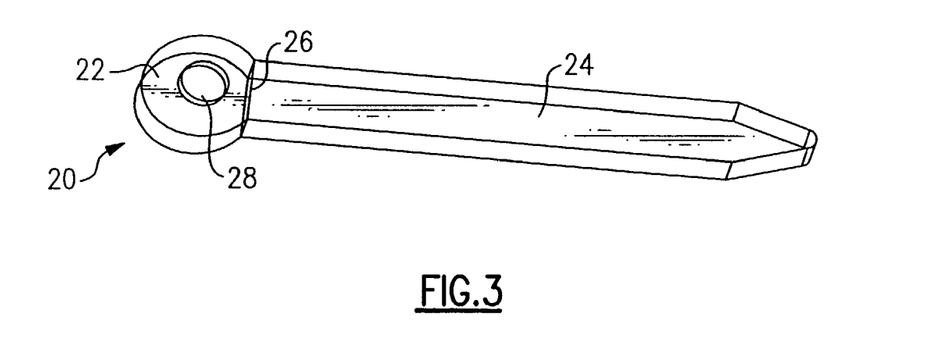
FIG. 3 is an enlarged view of a reaction and separating compartment of the disc of FIG. 1.

The body 12 defines a plurality of radially extending compartments 20 as illustrated in FIGS. 2 and 3. Each compartment 20 includes a reaction chamber 22 and a separation chamber or channel 24, FIG. 3. Material may be introduced into the reaction chamber 22 via an aperture 28 in the cover 14 of the device 10. The separation chamber or channel 24 may be preloaded with a medium which forms a density gradient on application of a centripetal force. This type of material may include, for example, a Percoll density medium.

In one embodiment of the present invention, the reaction chamber 22 is located closest to the center of the disc as illustrated in FIG. 2. The reaction chamber 22 is connected to the separation chamber 24 via a controllable barrier 26, FIG. 3, and the separation chamber is pre-loaded with a density gradient medium.

Figure 3A:
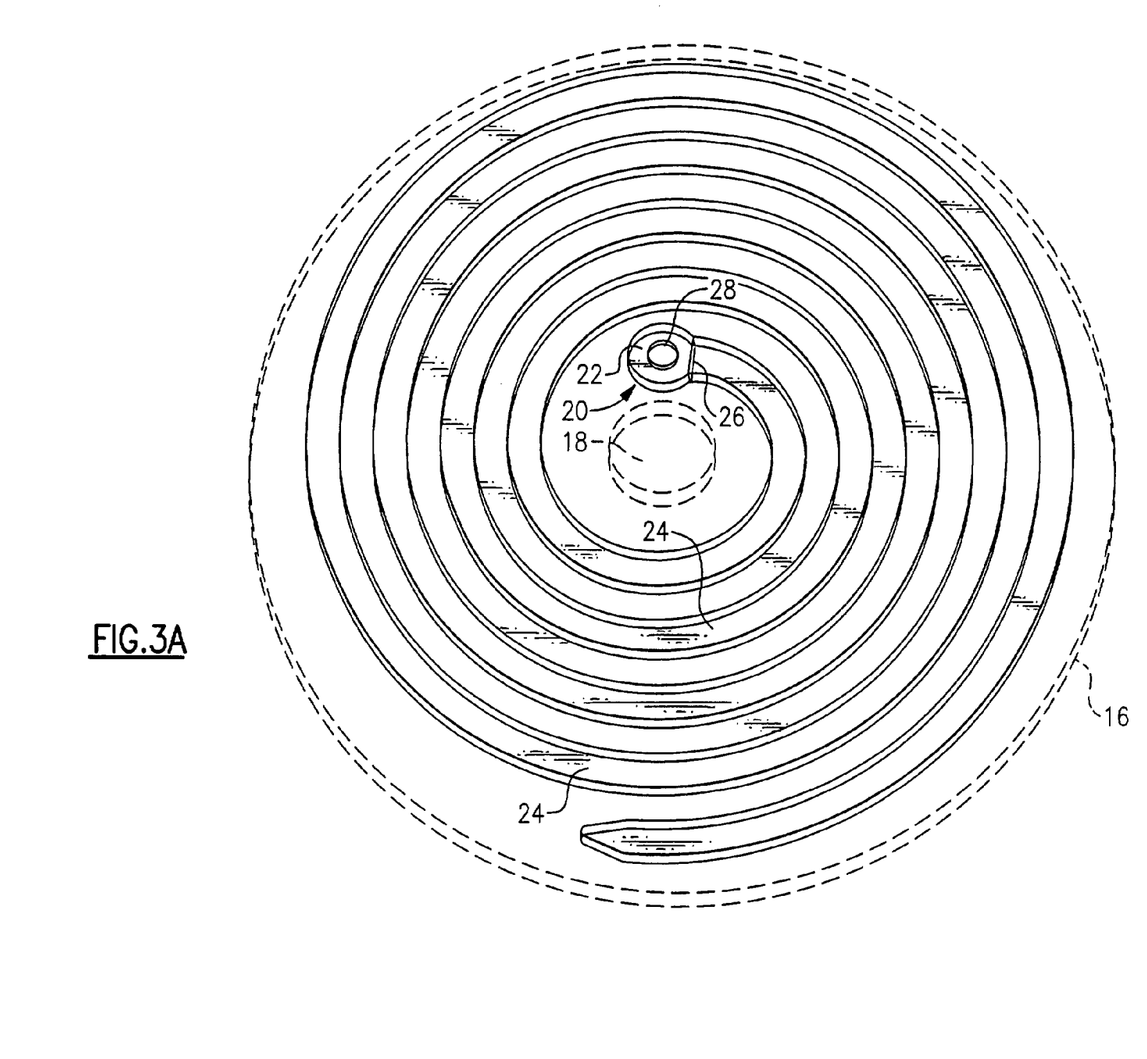
FIG. 3A presents a spiral implementation of the reaction and separating compartment of FIG. 3.
Figures 3B, 3C, 3D:
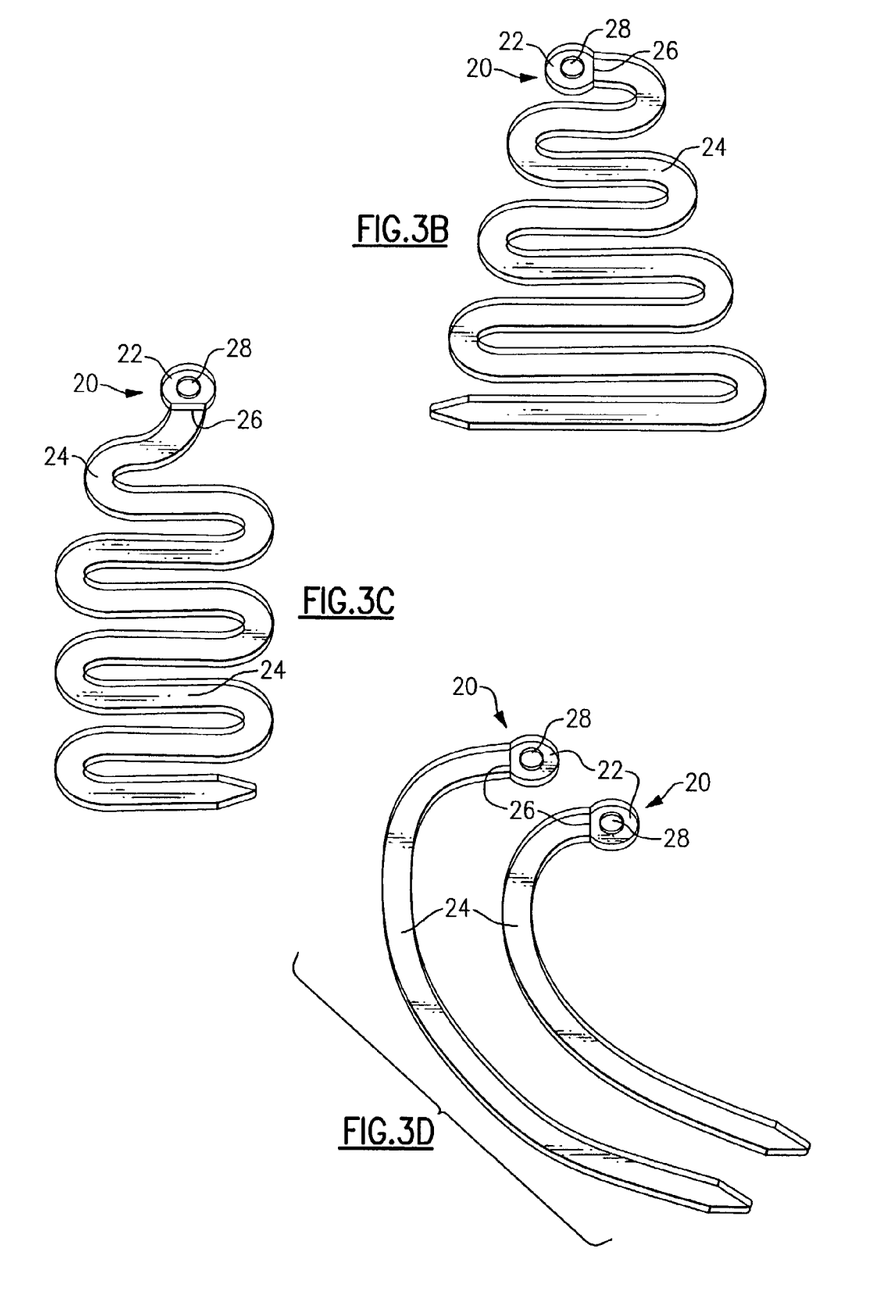
FIG. 3B illustrates a serpentine configuration of the reaction and separating compartment depicted in FIG. 3.
FIG. 3C shows a sinusoidal form of the reaction and separating compartment illustrated in FIG. 3.
FIG. 3D depicts an arcuate version of the reaction and separating compartment shown in FIG. 3.

According to an alternate embodiment of the separation chamber 24, the form thereof is spiral, FIG. 3A, rather than straight and radially directed. In this embodiment, a substantially longer chamber or channel is formed to thereby provide a finer gradation per unit length and thus increase in the resolution of the assay. This embodiment thus provides a disc-based density chromatography system also referred to herein as a "flow-through" system. Alternate implementations of this embodiment also include the serpentine configuration illustrated in FIG. 3B, the sinusoidal form shown in FIG. 3C, and the arcuate shape depicted in FIG. 3D. In the serpentine formation shown in FIG. 3B, each of the consecutive coils has an increasing diameter as illustrated. In this configuration, the individual coils may have a slight arc shape that conforms to the arc of the corresponding circumference at a respective point along a radius of the disc. In the sinusoidal configuration illustrated in FIG. 3C, each of the consecutive coils has substantially the same diameter. In the arcuate-shaped separation channel 24 depicted in FIG. 3D, the length thereof may span the entire radius of the disc so that the channel 24 extends essentially form the center of the disc to the outer edge. Alternatively, the length of the arcuate-shaped separation channel 24 shown in FIG. 3D, may span across only about half the radius of the disc, for example. In this configuration, two consecutive annuli of separation channels may be provided on the disc.

The "flow-through" system embodiment of the present invention is not limited to density gradient chromatography but may include any chromatography system including, for example, size exclusion, reverse phase, ion exchange, and affinity chromatography. Alternatively, the "flow-through" system may be used in a disc based flow cytometry application.

In another embodiment of the present invention, the compartment 20 orientation is reversed wherein the reaction chamber 22 is now located furthest from the center of the disc. This reverse reaction chamber configuration may be implemented in any of the embodiments of the separation channels 24 illustrated in FIGS. 3, 3A, 3B, 3C, and 3D. In these implementations, the reaction chamber 22 and the separation chamber 24 are in fluid communication with each other. The compartment 20 may be pre-loaded with a density medium or the medium may be prepared and mixed with micro-particles and assay solution off-disc and applied into the compartment for analysis. In the present embodiment a centripetal force creates and maintains the density gradient due to the properties of the medium. Once the gradient is formed the beads will then move and settle at their isopycnic points within the medium based on their individual buoyant densities. This reverse chamber system is herein referred to as the "buoyant density separation system".

Figure 4:
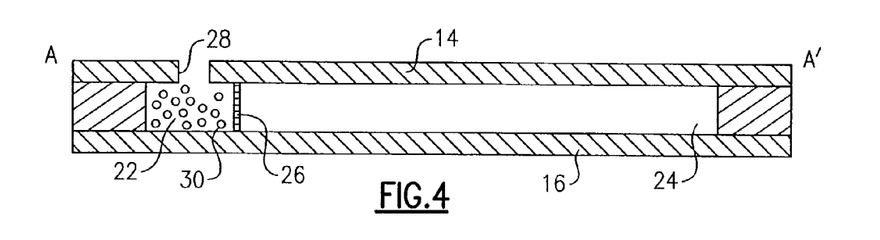
FIG. 4 is a diagrammatic sectional view along points A-A' through the compartment of the disc of FIG. 1.

Reference is now made to FIG. 4 which depicts a cross-sectional view of the disc 10 along the compartment 20. The reaction chamber 22 is separated from the separation chamber 24 by the controllable barrier 26. The barrier 26 may be formed from a frangible membrane that fractures once a centripetal force that exceeds a threshold value is applied. The reaction chamber 22 contains a plurality of beads 30 of different densities. In one embodiment of the invention, the reaction chamber 22 may also contain fluorescent anti-IgG. Aperture 28 allows introduction of a test sample into the reaction chamber 22.

The various antigen-antibody interactions that occur in the reaction chamber 22 will now be described with reference to FIGS. 5, 6, 7, and 8. The drawings depict beads or micro-particles 30a, 30b, and 30c, which are each of a different color according to one embodiment thereof. The beads 30a, 30b, or 30c are also of different densities, the bead 30a of FIG. 5 being the least dense, and the bead 30c of FIG. 7 being the most dense.

Figure 5:
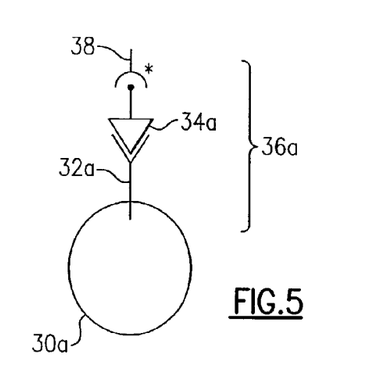
FIGS. 5 to 8 are schematic diagrams which illustrate the interactions occurring in embodiments of the present invention.
Figure 6:
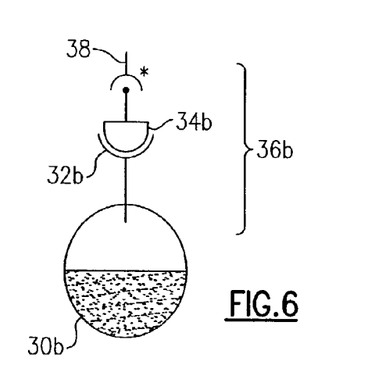
Figure 7:
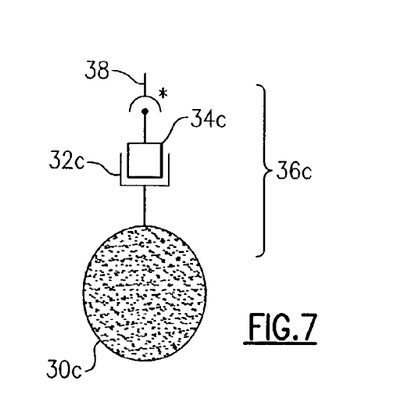

With reference now to FIGS. 5, 6, and 7, there is illustrated a sandwich type assay including at least one capture bead, one antigen or target agent, and one labeled tag bound in a complex by antigen-antibody interactions. Each capture bead 30a, 30b, or 30c has attached thereto a specific antibody or capture probe 32a, 32b, or 32c. The antibodies 32a, 32b, and 32c are specifically selected based on their affinity for antigens or target agents 34a, 34b, or 34c which may be present in the sample. The antibodies 32a, 32b, and 32c are immobilized on to the surface of the beads 30a, 30b, and 30c, respectively. As can be seen from FIGS. 5 through 8, any antigen 34a, 34b, or 34c present in the sample will bind specifically to the antibodies 32a, 32b, or 32c immobilized on the beads 30a, 30b, or 30c. A sandwich-type complex 36a, 36b, or 36c is formed when the fluorescent anti-IgG 38 binds to the bound antigens 34a, 34b, or 34c.

Figure 8:
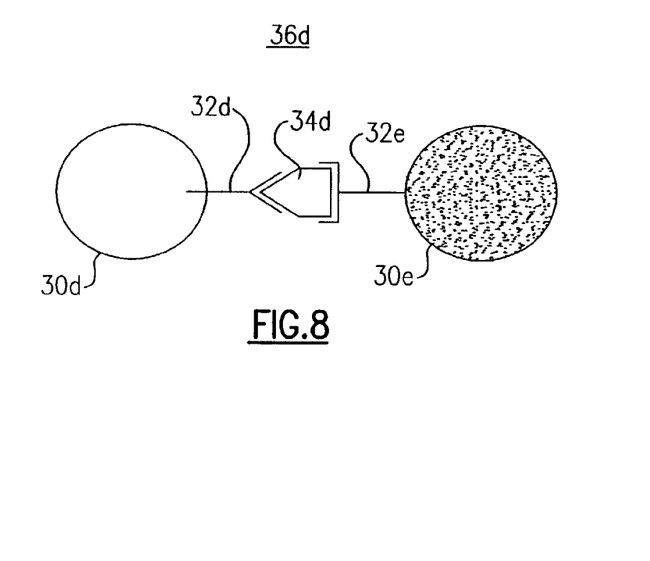

Referring specifically to FIG. 8 now, there is shown a binding partner bead or micro-particle complex 36d, including at least one capture bead or capture micro-particle 30e, one target agent 34d, and one reporter bead or reporter micro-particle 30d. The bead partner complex is formed by the specific binding of the target antigen or target agent 34d to capture probe 32e and reporter probe 32d that are bound to bead binding partners 30e and 30d, respectively. Probes 32d and 32e each have affinity to different epitopes on target 34d and no affinity for each other. The resulting binding partner bead complex 36d formed in this sandwich assay has a density approximately equal to the average densities of the two beads 30d and 30e. Thus when the binding partner bead complex 36d is introduced into the density gradient medium in the separation chamber 24 (FIGS. 3, 3A, 3B, 3C, and 3D), the complex will come to rest at an isopycnic point between the uncomplexed beads 30d and 30e. Alternatively, one of the bead binding partners, may be a cell binding partner wherein the capture bead 30e or reporter bead 30d has probes that have specific affinity to cell surface markers on the cell as discussed above and in conjunction with FIG. 12 below.

Operation of the device 10 is now described with reference to FIGS. 9, 10, 11, and 12. For the sake of clarity, the complexes 36a, 36b, and 36c have been omitted from the drawing figures. These complexes will now be referred to by their respective bead numbers as shown in FIGS. 5, 6, and 7.

Figure 9:
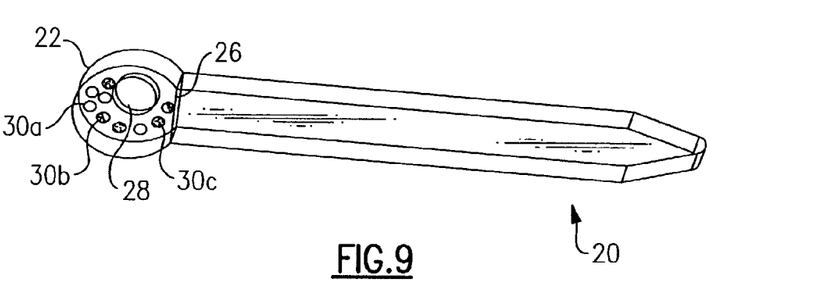
FIGS. 9 to 12 are diagrammatic representations of the compartment of FIG. 3 illustrating an embodiment of the present invention in operation.

Referring first to FIG. 9, there is depicted a compartment 20 which is loaded and ready for use. In this embodiment, the reaction chamber 22 contains fluorescent anti-IgG and capture beads 30a, 30b, and 30c of different densities. The controllable barrier 26 prevents material in the reaction chamber 22 from moving into the separation chamber 24.

Figure 10:
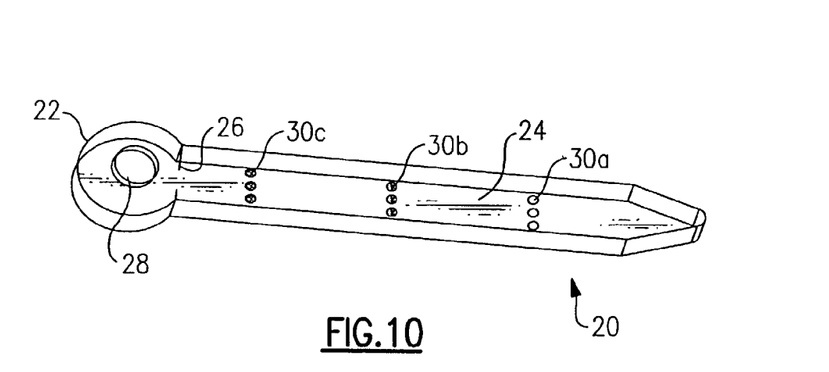

By way of example, and not limitation, a sample of blood serum is introduced into the reaction chamber 22. If antibodies or target agents 34a, 34b, or 34c are present in the sample, they will bind to the immobilized antigens or capture probes 32a, 32b, or 32c and the fluorescent anti-IgG 38 to form the sandwich-type complexes 36a, 36b, or 36c depicted in FIGS. 5, 6, and 7. The disc 10 is then rotated. A density gradient is formed in a density medium including Percoll medium. In this embodiment, the medium is at its densest closest to the center of the disc 10. Once the disc 10 is rotated above a threshold speed and the centripetal force exceeds a threshold value, the controllable barrier 26 fractures, as shown in FIG. 10.

The beads 30a, 30b, and 30c, in response to the centripetal force, move from the reaction chamber 22 to the separation chamber 24. The beads 30a, 30b, and 30c travel along the length of the separation chamber 24 and come to the rest at their isopycnic points. As defined above, a bead 30a, 30b, or 30c reaches its isopycnic point when its density equals that of its surrounding medium. The precise location of a bead's isopycnic point is dependent upon its density. Accordingly, the bead 30a of FIG. 5 will come to rest furthest away from the center of the disc. In contrast, the densest beads 30c of FIG. 7 come to rest closest to the center of the disc.

Unreacted material (i.e. unreacted sample and unreacted fluorescent anti-IgG), being less dense than the Percoll medium, remains within the reaction chamber 22.

Figure 11:
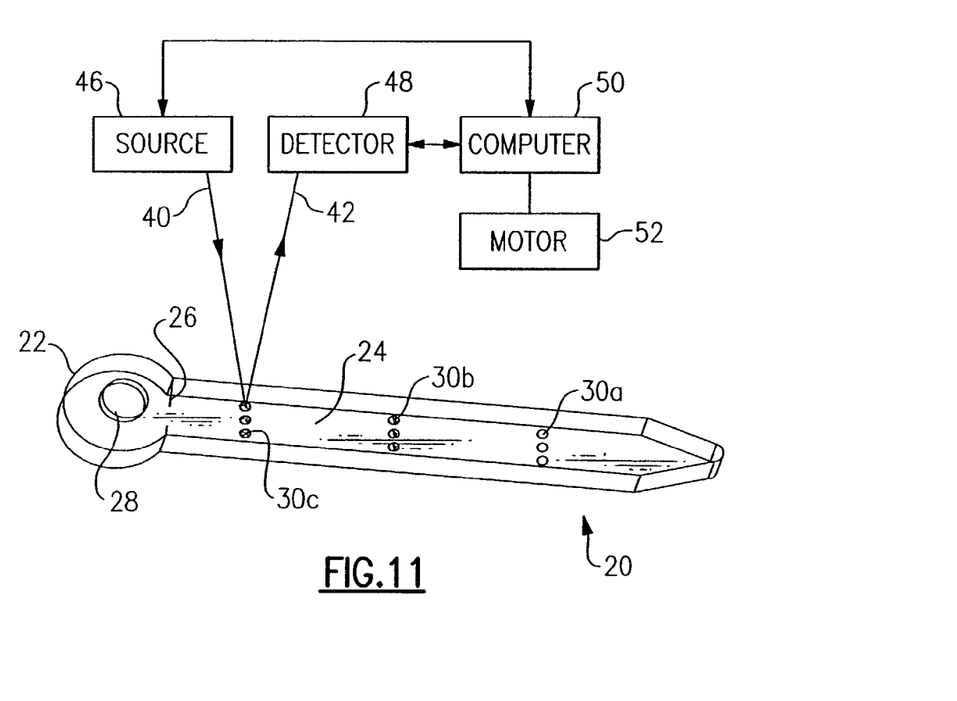

As shown in FIG. 11, the capture beads 30a, 30b, and 30c are separated in a density gradient, including Percoll medium, into various bands. These bands fluoresce due to the presence of fluorescent anti-IgG 38. The position of beads 30a, 30b, and 30c may be measured by using a disc-based scanning device of the type described, for example, in incorporated U.S. Pat. No. 5,892,577 or any suitable fluorescent type optical disc reader or scanner.

Figure 12:
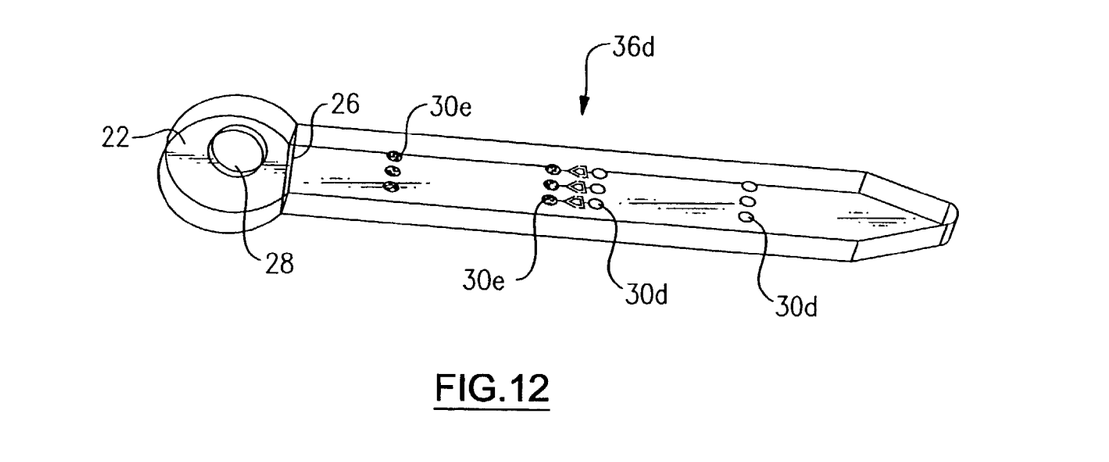

Similarly, FIG. 12 shows a sandwich-type assay using two binding partners including beads of different densities and/or sizes formed as described above and shown in FIG. 8. As discussed in conjunction with FIG. 8 and shown here in FIG. 12, the resulting binding partner bead complex has an isopycnic point between the isopycnic points of the individual component beads. When the disc is rotated, the beads migrate in the density gradient and come to rest at their respective isopycnic points. Thus complex 36d will come to rest between uncomplexed beads 30d and 30e. As mentioned above, bead complex formation is not limited to binding partner bead complexes but may contain complexes with three or more different binding partners. The resulting complex will have an isopycnic point equal to the average of the isopycnic points of all the binding partners in the complex. The binding partners are also not limited to beads but may include beads, cells, and labels or tags in any combination.

Referring again to FIG. 11, whilst the disc 10 is rotating, a beam 40 of electromagnetic radiation from a source 46 may be scanned over the cover 14 of the disc 10. The beam 40 is transmitted through the cover 14 and interacts with material in the separation chamber 24. An interacted, return, or "modulated" beam 42 is detected by a detector 48 and can then be analyzed by a computer 50 or other analyzer. The analysis can provide information on the position of incident beam 40 and/or information on the nature of the material under analysis. The disc can include other types of testing chambers and can have software readable by the system. Such software can instruct the computer in operation, e.g., to control the source 46 to direct light with specific characteristics, or to control a motor 52 that rotates the disc including disc speed, direction, and acceleration. In another embodiment, where the disc is assembled in a reverse manner, as discussed in conjunction with FIG. 1, the beam of electromagnetic radiation may be scanned from the bottom side of the disc through the base 16 and over the cover 14. In yet another embodiment, the beam may be allowed to pass through the disc assembly and detected by a detector located on the opposite side from the beam source. Details regarding this embodiment are described in conjunction with U.S. Pat. No. 5,892,577.

In a further alternate embodiment of the present invention, the incident beam is held stationary. According to a method of this alternate embodiment, there is provided the step of directing an incident beam of electromagnetic radiation on a fixed point within the separation chamber. This method also includes the step of detecting the micro-particles or the labeled tags while the particles flow through the separation chamber to thereby determine sedimentation rate or elution time of the micro-particles through the medium. This advantageously also allows for the determination of the presence and amount of any target bound to the micro-particles. This method of separating and detecting micro-particles or cells by time is herein referred to as the "flow-through" system which is similar to a density chromatography system.

Fluorescent anti-IgG, the beads, the bead complexes, or bead-cell complexes interact with the incident beam in a characteristic manner to produce a characteristic modulated signal. Thus, by monitoring these characteristic modulated signals, the precise location and amount of the beads, bead complexes, and bead-cell complexes may be determined. By comparing these results with the results of a control experiment, the identity and quantity of the antigens present in the sample under test may be deduced.

In another embodiment, the device of the present invention may be used to analyze a sample for antibodies. Here, specific antigens may be immobilized onto the beads. A sample containing target antibodies is mixed with the antigen-bound beads and labeled reagents such as fluorescent IgG. The IgG has an affinity for a portion of the antibody, such as the Fc portion. The signal from the bound IgG may then be used to detect the antibody of interest bound to the antigen on the bead. Non-limiting examples of antigens which may be immobilized onto beads include viral antigens as from hepatitis (e.g., U.S. Pat. No. 6,312,889), herpes (e.g., U.S. Pat. No. 6,126,944), or HIV (e.g., U.S. Pat. No. 5,834,267); bacterial antigens as from *M. tuberculosis* (e.g., U.S. Pat. No. 6,245,331) or *Bacillus anthracis* (e.g., U.S. Pat. No. 5,677,274); parasitic antigens as from *Plasmodium* (e.g., U.S. Pat. No. 6,120,770), *M. leprae* (e.g., U.S. Pat. No. 4,906,742), or *Leichmania* (e.g., U.S. Pat. No. 5,411,865); also disease marker antigens as for cancer (e.g., U.S. Pat. Nos. 6,350,583 and 6,242,203).

Several embodiments herein utilize the immunloglobulin IgG for capture and/or detection purposes. Other immunloglobulins, such as IgM, IgA, IgE, may also be used for capture and/or detection purposes. Moreover, immunoglobulins that are used by the assays of the invention can be polyclonal antibodies or monoclonal antibodies or recombinant antibodies or fragments thereof.

It should be noted that the systems and methods of the present invention are not limited to antigen-antibody interaction. Any moieties that are capable of being binding partners may be used in this invention. By way of non-limiting example, one embodiment of the present invention uses a receptor protein that is bound to the beads, which when exposed to a sample will bind its respective ligand. The receptor-bound ligand attached to the beads may then be detected by the use of a labeled reagent such as fluorescent IgG that is specific for the ligand. Alternatively, the presence of the ligand may also be detected through the formation of a binding partner bead complex by use of a second bead with another receptor protein with an affinity for a different portion of the same ligand. In another example, the assay can be based on enzyme/substrate interaction, such that the enzyme or substrate is bound to the bead. Detection of either the enzyme or substrate can then be accomplished using an immunoglobulin of appropriate specificity for either molecule that is appropriately labeled. Alternatively, the detection of the enzyme that is bound to the bead may be carried out using an appropriate substrate that reacts with the enzyme to produce a detectable product such as color or fluorescence. If the substrate is the target that is captured by the bead, then an appropriate enzyme may be introduced to the assay mix that interacts with the substrate to produce a detectable product. In yet another embodiment, antibodies can be excluded completely from the assay. Beads can be coated with a lectin molecule that will specifically bind a particular carbohydrate moiety in a sample. Detection of the bound carbohydrate may then be accomplished with a labeled second lectin that also binds the carbohydrate or a second bead with a lectin that also binds to the carbohydrate.

Also envisioned is the use of the assay for the detection of specific sequences of nucleic acids including DNA or RNA. By way of example, and not limitation, a sense or antisense strand can be immobilized on the beads and exposed to a sample. If the corresponding sense or antisense molecule is present in the sample, it will bind to the oligonucleotide probe that is bound to the beads after an appropriate period of time under conditions that promote hydrogen bonding between the sense and antisense molecules. Detection may then be accomplished by exposing the complex to an appropriately labeled marker such as an antibody or a third nucleic acid molecule that will hybridize only to the nucleic acid molecule being screened for in the sample. Alternatively, the antibody or the third nucleic acid molecule can be bound to another bead (a binding partner) of a different density and electromagnetic property. The resulting bead complex can then be detected by the incident beam as discussed above in connection with FIGS. 8, 11, and 12.

Various modifications or alterations may be made to the embodiments described above without departing from the scope of the present invention. For example, the controllable barrier may be mechanically or electronically controlled. Alternatively, the barrier may take the form of a raised protrusion disposed between the separation chamber and reaction chamber. In this embodiment, material may only pass from the reaction chamber to the separation chamber once the device rotates above a threshold speed. Below this threshold, the centripetal force is insufficient to draw material over the protrusion. The rotation that is employed can be clockwise or counterclockwise, or alternated in stages when it is desired to move or agitate the assay solution in a particular direction or manner. While the description above has been in terms of biological examples, a sample could be tested for chemical purposes, such as testing water for particular impurity including toxic metals, organic toxins, or inorganic toxins.

CONCLUDING SUMMARY

The methods and apparatus discussed herein may be readily adapted to, used in combination with, or implemented in conjunction with any of the methods, systems, and devices disclosed in, for example, the following commonly assigned and co-pending applications or issued patents: U.S. patent application Ser. No. 09/284,421 entitled "Apparatus and Methods for Conducting Assays" filed Jun. 11, 1999; U.S. patent application Ser. No. 09/394,137 entitled "Spatially Addressable, Cleavable Reflective Signal Elements, Assay Device and Method" filed Sep. 10, 1999, now U.S. Pat. No. 6,312,901; U.S. patent application Ser. No. 09/120,049 entitled "Optical Disk-based Assay Devices and Methods" filed Jul. 21, 1998, now U.S. Pat. No. 6,342,349; U.S. patent application Ser. No. 09/064,636 entitled "Laboratory in a Disk" filed Apr. 21, 1998, now U.S. Pat. No. 6,030,581; U.S. patent application Ser. No. 09/421,870 entitled "Trackable Optical Discs with Concurrently Readable Nonoperational Structures" filed Oct. 26, 1999; U.S. patent application Ser. No. 09/988,728 entitled "Methods and Apparatus for Detecting and Quantifying Lymphocytes with Optical Biodiscs" filed Nov. 20, 2001; U.S. patent application Ser. No. 10/038,297 entitled "Dual Bead Assays Including Covalent Linkages For Improved Specificity And Related Optical Analysis Discs" filed Jan. 4, 2002; U.S. patent application Ser. No. 10/099,256 entitled "Dual Bead Assays Using Cleavable Spacers and/or Ligation to Improve Specificity and Sensitivity Including Related Methods and Apparatus" filed Mar. 14, 2002; and U.S. patent application Ser. No. 10/099,266 entitled "Use of Restriction Enzymes and Other Chemical Methods to Decrease Non-Specific Binding in Dual Bead Assays and Related Bio-Discs, Methods, and System Apparatus for Detecting Medical Targets" filed Mar. 14, 2002, all of which are herein incorporated by reference in their entireties.

All other patents, patent applications, and publications mentioned in this specification are also incorporated herein in their entireties by reference.

While this invention has been described in detail with reference to certain preferred embodiments and technical examples, it should be appreciated that the present invention is not limited to those precise embodiments or examples. Rather, in view of the present disclosure, which describes the current best mode for practicing the invention, many modifications and variations would present themselves to those of skill in the art without departing from the scope and spirit of this invention. For example, as discussed above, separating and detecting micro-particles or cells by time in a density chromatography format or a "flow-through" system is contemplated by the present invention. In this implementation of the invention, the micro-particles or cells are denser than the density medium. Upon application of a centrifugal force, the micro-particles or cells move and are separated in the density medium according to their sedimentation rate. The micro-particles or cells may then be detected as they move past a fixed detector. The different micro-particles or cells may also be tagged with different labels to aid in the detection and identification of different species present in the sample. This aspect of the present invention may also be implemented in combination with the buoyant density system described above wherein some micro-particles or cells may not be dense enough to flow through the entire length of the separation chamber but may remain at their isopycnic points. These particles may then be detected by moving the detector to different areas within the separation chamber as described above. The scope of the invention is, therefore, indicated by the following claims rather than by the foregoing description. All changes, modifications, and variations coming within the meaning and range of equivalency of the claims are to be considered within their scope.

What is claimed is:

1. A disc system for conducting an assay on a sample, comprising;
   a rotatable disc with a chamber for receiving the sample;
   a plurality of beads in the chamber including at least two different groups of beads, each of the beads in each group having a common physical characteristic and having attached thereto at least one capture probe with affinity to a specific target;
   wherein said common physical characteristic of the beads of one group is different from the physical characteristic associated with the other groups;
   wherein said physical characteristic comprises density; and
   a medium in the chamber for forming a density gradient in response to rotation of the disc such that different locations in said medium have density that substantially matches the density of beads in one of said groups of beads so that rotation of the disc causes beads from the different groups to move radially within the medium to the locations where the density of the beads substantially matches the density of the medium, said beads thereby coming to rest at different locations in the chamber.

2. The system according to claim 1 wherein said physical characteristic further comprises bead size.

3. The system according to claim 1 wherein said physical characteristic further comprises color.

4. The system according to claim 1 wherein said physical characteristic further comprises a pre-determined fluorescent characteristic.

5. The system of claim 1 wherein the rotatable disc includes an upper cover disc, a base, and a body disposed between the cover and the base, the body defining the chamber.

6. The system of claim 1 wherein the chamber has two sub-chambers with a controllable barrier therebetween, said controllable barrier being controlled by centripetal forces.

7. The system of claim 1 wherein the chamber has two sub-chambers with a controllable barrier therebetween, said controllable barrier being controlled by electrical or mechanical means.

8. The system of claim 1 wherein the capture probe is selected from the group comprising antigens, antibodies, DNA, RNA, lectins, protein receptors, ligands, biotin, and streptavidin.

9. The system of claim 1 wherein the density gradient in the medium is formed by application of centripetal force when the disc is rotated.

10. The system of claim 1 further comprising a detection assembly including a radiation source and a detector for detecting radiation modulated by the sample.

11. The system of claim 10 wherein the radiation source includes a laser.

12. The disc system of claim 1 wherein each of said beads moving radially within the medium comes to rest at its isopycnic point.

13. A disc system for conducting an assay on a sample, comprising:

a rotatable disc with a chamber for receiving the sample;

a first bead having a first density and a second bead having a second density that is different than the first density, each of the first and second beads being in the chamber and having attached thereto at least one captive probe with affinity to a specific target; and a medium in the chamber, said medium for forming a density gradient in response to rotation of the disc, such that when the disc is rotated the first and second beads move radially within the medium in an amount that is a function of the first or second density and the density gradient so as to come to rest at different radial locations within the chamber.

14. The system of claim 13 wherein the chamber has two sub-chambers with a controllable barrier therebetween, said controllable barrier being controlled by centripetal forces.

15. The system of claim 13 wherein the chamber has two sub-chambers with a controllable barrier therebetween, said controllable barrier being controlled by electrical or mechanical means.

16. The system of claim 13 wherein the density gradient in the medium is formed by application of centripetal force when the disc is rotated.

17. The disc system of claim 13 wherein each of said first and second beads moving radially within the medium comes to rest at its' isopycnic point.

* * * * *